United States Patent
Chavan et al.

(10) Patent No.: US 8,940,343 B2
(45) Date of Patent: Jan. 27, 2015

(54) PERSONAL CARE COMPOSITION

(75) Inventors: Mohan Vijaykumar Chavan, Mumbai (IN); Deepak Ramachandra Mhasavade, Bangalore (IN); Ashish Anant Vaidya, Bangalore (IN)

(73) Assignee: Conopco Inc., Englewood Cliffs, NJ (US)

( * ) Notice: Subject to any disclaimer, the term of this patent is extended or adjusted under 35 U.S.C. 154(b) by 164 days.

(21) Appl. No.: 13/637,464

(22) PCT Filed: Apr. 1, 2011

(86) PCT No.: PCT/EP2011/055082
§ 371 (c)(1),
(2), (4) Date: Nov. 16, 2012

(87) PCT Pub. No.: WO2011/124528
PCT Pub. Date: Oct. 13, 2011

(65) Prior Publication Data
US 2013/0052148 A1 Feb. 28, 2013

(30) Foreign Application Priority Data
Apr. 6, 2010 (IN) .................. 1145/MUM/2010

(51) Int. Cl.
| | |
|---|---|
| *A61K 36/82* | (2006.01) |
| *A61Q 17/04* | (2006.01) |
| *A61K 8/35* | (2006.01) |
| *A61K 8/49* | (2006.01) |
| *A61K 8/894* | (2006.01) |
| *A61K 8/97* | (2006.01) |
| *A61Q 5/00* | (2006.01) |

(52) U.S. Cl.
CPC . *A61Q 17/04* (2013.01); *A61K 8/35* (2013.01); *A61K 8/498* (2013.01); *A61K 8/894* (2013.01); *A61K 8/97* (2013.01); *A61K 2800/52* (2013.01); *A61Q 5/00* (2013.01)
USPC ............................................ 424/729; 424/59

(58) Field of Classification Search
USPC ................................................ 424/729, 59
See application file for complete search history.

(56) References Cited

U.S. PATENT DOCUMENTS

| | | | |
|---|---|---|---|
| 5,306,486 A | 4/1994 | McCook | |
| 5,952,391 A | 9/1999 | Gers-Barlag | |
| 6,024,944 A | 2/2000 | Hansenne | |
| 2006/0275241 A1 | 12/2006 | Padlo | |
| 2008/0102045 A1* | 5/2008 | Shim | ................................ 424/59 |
| 2009/0092690 A1 | 4/2009 | Yang | |

FOREIGN PATENT DOCUMENTS

| | | |
|---|---|---|
| EP | 1092414 | 4/2001 |
| EP | 1092414 A2 | 4/2001 |
| EP | 1640041 | 3/2012 |
| WO | W02009040194 | 4/2009 |

OTHER PUBLICATIONS

Luczaj, W. et al., "Antioxidativae properties of black tea", Preventive Medicine, 40 (2005) pp. 910-918.*
Vermeer et al., "Theaflavins from Black Tea, Especially Theaflavin-3-gallate, Reduce the Incorporation of Cholesterol into Mixed Micelles", Journal of Agricultural and Food Chemistry, 2008, vol. 56, pp. 12031-12036.
PCT International Search Report in PCT application PCT/EP2011/055082 dated Apr. 3, 2012 with Written Opinion.
International Preliminary Report on Patentability in PCTEP2011055082, dated Aug. 20, 2012.
Jayabalan et al., "Changes in content of organic acids and tea polyphenols during kombucha tea fermentation", 2007, vol. 102, No. 1, pp. 392-398.
Lakenbrink et al., Flavonoids and Other Polyphenols in Consumer Brews of Tea and Other Caffeinated Beverages, Journal of Agric. Food Chem 2000 48 2848, 2000, 2848-2852, 48.
Starch et al., "Expanding Silicone Technologies for Sun Care: Performance Complements Aesthetics", Dow Corning, 1210712008, 1-21, Form No. 27/1303.
Mintel, "Anti-Ageing Hand Treatment SPF 20", Jun. 2010 (XP-002622098).
Rice-Evans et al., "Antioxidant properties of phenolic compounds", Trends in plant science reviews, Apr. 1997, vol. 2, No. 4, pp. 152-159.
European Searh Report in Ep application EP10 173 852 dated Feb. 15, 2011 with Written Opinion.

* cited by examiner

Primary Examiner — Gina Justice
(74) Attorney, Agent, or Firm — Rimma Mitelman

(57) ABSTRACT

The present invention relates to a personal care composition. More particularly the present invention relates to stabilization of UVA sunscreen dibenzoylmethane derivatives or even more particularly Parsol 1789™ (4-t-butyl-4'-methoxydibenzoylmethane) in personal care compositions. It is an object of the present invention to provide a personal care composition with relatively long photoprotection efficiency. It is another object of the present invention to stabilize Parsol 1789 by use of a natural substance or materials derived from plants. Surprisingly the present inventors have found that theaflavin or black tea extract having high levels of theaflavin, can act as a photostabilizer for dibenzoylmethane derivatives or Parsol-1789™.

13 Claims, No Drawings

US 8,940,343 B2

PERSONAL CARE COMPOSITION

TECHNICAL FIELD

The present invention relates to a personal care compositions. More particularly, the present invention relates to improving the stability of UVA sunscreen dibenzoylmethane derivatives or even more particularly Parsol 1789™ (4-t-butyl-4'-methoxydibenzoylmethane) in personal care compositions.

BACKGROUND OF THE INVENTION

In today's polluting world and outdoor lifestyle most consumers want to protect their skin, hair and scalp from harmful ultraviolet rays emitted by sun. That makes skin protection sector very important for consumer goods companies.

Consumers from different parts of the world have different characteristics of their skin. This is attributed to their genetic structure and geographical conditions. But invariably almost all consumers from different part of the world want to protect their skin, hair and scalp from harmful UV rays while exposing themselves to sunlight.

There are several ways by which consumers may obtain photoprotection of skin from sunlight especially from UV radiation. Sunscreens/sunblocks are generally used for this purpose. Sunscreens are generally organic molecules that absorb the UV radiation and emit the energy in a different form, for instance in the visible range of the spectrum or in the form of heat, thereby protecting the skin against irritation and sunburn. Sunscreens are generally small organic molecules.

Similarly sunblocks help to protect the skin against possible irritation and sunburn. These sunblocks generally comprise inorganic particulates (like ZnO, $TiO_2$) that reflect the incident UV-visible rays thus protecting the skin.

Formulations using these molecules in the form of a cream, a lotion, gel, or spray are widely known in the industry.

People have also tried to use other natural substances (like green tea extract or other herbs extracts) alone or along with a chemical sunscreen for effective photoprotection of skin.

One of these chemical sunscreen is a derivative of dibenzoylmethane which is known as 4-t-butyl-4'-methoxydibenzoylmethane sold as Parsol 1789™ (or Avobenzone™), is a well known UVA sunscreen used in personal care composition. The problem associated with this sunscreen is its relatively unstable nature. Efforts have been made to add some external molecule, like Octocrylene™, to improve stability of Parsol 1789 in formulations. Investigations are ongoing throughout the world to find other alternatives to improve stability and the photoprotection efficiency of Parsol 1789™.

So there is a need to develop a personal care composition with improved stability of dibenzoylmethane derivative or Parsol 1789™.

U.S. Pat. No. 5,306,486 (McCook et al., 1994) describes a cosmetic composition including green tea and a sunscreen compound which is effective to at least partially block ultraviolet radiation from harming human skin.

US 2006/0275241 (Padlo et al., 2006) describes a cosmetic towelette product which includes a water-insoluble substrate and cosmetic composition in contact with the substrate. The composition includes a copolymer structured from in part a vinyl ester of a $C_3$-$C_{20}$ acid and a tea extract delivered in a cosmetically acceptable carrier. The combinations of copolymer and tea extract ensure that color changes in the product are minimized.

EP 1 640 041 (Henkel, 2006) discloses cosmetic skin treatment agents, primarily providing anti-ageing benefits, in the form of an oil-in-water emulsion, the emulsion containing taurine and at least one linear primary fatty or wax alcohol having an alkyl chain length of 20-40 carbon atoms. Examples are disclosed in this patent publication where dibenzoylmethane sunscreens and Kombucha are present in skin care compositions. Kombucha is a fermented tea beverage produced by fermenting sugared black tea with tea fungus (Food Chemistry, 102 (2007) 392-398). Kombucha is generally available from Sederma under the brandname Kombuchka™. Kombucha or Kombuchka™ is usually added in skin care composition at about 1 to 3% w/w. Being a black tea extract based product, Kombucha typically comprises from about 1% to a maximum of 2.8% theaflavin. Thus such skin care compositions comprising Kombucha generally comprise 0.01 to a maximum of 0.09% w/w theaflavin. The present inventors have determined that the benefits of the present invention cannot be obtained by inclusion of such low amounts of theaflavin Surprisingly, the present inventors have found that theaflavin or black tea extract having higher levels of theaflavin, can act as a photostabilizer for dibenzoylmethane derivatives or Parsol-1789™. Aqueous extract of black tea typically contains a minimum of 0.1 to a maximum of about 2.8% w/w theaflavin and in rare cases up to 3% w/w theaflavin. Most black tea extracts contain theaflavin from 1 to 2% w/w (Vermeer et al., J. Agric. Food Chem, 56, 12031-36 (2008)).

OBJECTS OF THE INVENTION

It is an object of the present invention to provide a personal care composition with relatively stabilized Parsol 1789.

It is another object of the present invention to provide a personal care composition with relatively long photoprotection efficiency.

It is yet a further object of the present invention to stabilize Parsol 1789 by use of a natural substance or materials derived from plants.

SUMMARY OF THE INVENTION

Accordingly the present invention provides a personal care composition comprising:
 i) a dibenzoylmethane derivative;
 ii) 0.1 to 30% by weight theaflavin; and,
 iii) a cosmetically acceptable base.

In another aspect the present invention provides a composition according to the invention for photoprotection of human skin.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of". It is noted that the examples given in the description below are intended to clarify the invention and are not intended to limit the invention to those examples per se. Similarly, all percentages are weight/weight percentages unless otherwise indicated. All amounts are by weight of the final composition, unless otherwise specified. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. The disclosure of the invention as found herein is to be considered to cover all embodiments as found in the claims as being multiply dependent upon each other irrespective of the fact that claims may be found without multiple dependency or redundancy.

"Personal Care Composition" as used herein, is meant to include a composition for topical application to skin and/or hair of mammals, especially humans. Such a composition may be generally classified as leave-on or rinse off, and includes any product applied to a human body for improving appearance, cleansing, odor control or general aesthetics with the principal aim being sun-protection in the present invention. The composition of the present invention can be in the form of a liquid, lotion, cream, foam, scrub, gel, soap bar or toner, or applied with an implement or via a face mask, pad or patch. Non-limiting examples of personal care compositions include leave-on skin lotions and creams, shampoos, conditioners, shower gels, toilet bars, antiperspirants, deodorants, lipsticks, foundations, mascara, sunless tanners and sunscreen lotions.

"Skin" as used herein is meant to include skin on the face and body (e.g., neck, chest, back, arms, underarms, hands, legs, buttocks and scalp). The composition of the invention is also of relevance to applications on any other keratinous substrate of the human body other than skin e.g. hair where products may be formulated with specific aim of providing photoprotection.

The ultraviolet (UV) portion of solar radiation is divided into three ranges based on wavelength viz. UVC (200-280 nm), UVB (280-320 nm) and UVA (320-400 nm). In a photoprotection formulation people generally use both UVA and UVB sunscreen as most of the UVC gets absorbed by the ozone layer.

As per the present invention the personal care composition comprises a dibenzoylmethane derivative, theaflavin and a cosmetically acceptable base. 4-t-butyl-4'-methoxydibenzoylmethane is selected as one of the dibenzoylmethane derivatives for the purpose of the present invention.

4-t-butyl-4'-methoxydibenzoylmethane is one of the very well known dibenzoylmethane derivative which is a sunscreen agent commonly known as Avobenzone™ or Parsol 1789™. Most of the consumer care products that intend to protect the substrate against UV radiation use Parsol 1789. Avobenzone™ is also available in the trade name of Parsol 1789™, Eusolex 9020™, Escalol 517™ and many others. This is an oil soluble ingredient used in sunscreen products to provide protection against the full spectrum of UVA rays. Avobenzone exists in the ground state as a mixture of the enol and keto forms, favoring the chelated enol. It is able to absorb ultraviolet light over a wider range of wavelengths compared to many organic sunscreen agents. That is the reason it is called as "broad spectrum" sunscreen. Avobenzone has an absorption maximum of 357 nm.

According to the invention, the personal care composition preferably comprises 0.1 to 10% dibenzoylmethane derivative, more preferably 0.1 to 4% by weight of the composition.

The personal care composition of the invention optionally can have other UVB sunscreens also like para-methoxy cinnamic acid and its derivative e.g. ethylhexyl methoxycinnamate which is known as Parsol MCX™, to protect entire gamut of UV rays. According to the invention, the personal care composition optionally comprises 0.1 to 10%, preferably 0.1 to 6% ethylhexyl methoxycinnamate by weight of the composition. Inclusion of p-methoxycinnamic acid derivative is especially useful since in addition to providing the known UV-B protection, the personal care composition ensures better stability of Parsol 1789 in the presence of p-methoxycinnamic acid derivative.

The present invention is about the stabilization of dibenzoylmethane derivative or Avobenzone by theaflavin. Throughout this specification, the word 'theaflavin' when used in the singular is intended to denote theaflavin (TF1) or its derivative (preferably TF2 to TF4), either singly or in any combination. Theaflavin (TF1) and its derivatives, usually known collectively in the plural as theaflavins, are antioxidant polyphenols, that are formed from catechins present in tea leaves during the enzymatic oxidation of tea leaves, to form black tea. Theaflavin are types of thearubigins, and are therefore reddish in color. Theaflavin are not found in green tea in any perceptible amount. In the manufacture of black tea, the monomeric flavan-3-ols undergo polyphenol oxidase-dependent oxidative polymerization, leading to the formation of bisflavanols, theaflavin, thearubigins and other oligomers in an oxidation process commonly known as "fermentation".

Theaflavin (typically present at about 1-2% w/w of the total extractable dry matter of black tea), includes theaflavin, theaflavin-3-gallate, theaflavin-3'-gallate, and theaflavin-3, 3'-digallate, possess benzotropolone rings with dihydroxy- or trihydroxy-substitution systems (as shown in FIG. 1), which give the characteristic color and taste of black tea.

Structure of Theaflavins

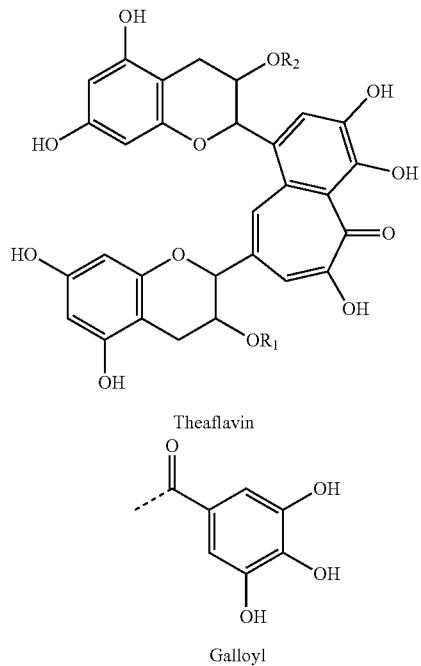

FIG. 1

The following table indicates the different types of theaflavin with respect to $R_1$ and $R_2$:

| Theaflavin | $R_1$ | $R_2$ |
| --- | --- | --- |
| Theaflavin (TF1) | H | H |
| theaflavin-3-gallate (TF2) | H | Galloyl |

-continued

| Theaflavin | $R_1$ | $R_2$ |
|---|---|---|
| theaflavin-3'-gallate (TF3) | Galloyl | H |
| theaflavin-3,3'-digallate (TF4) | Galloyl | Galloyl |

In one of the preferred embodiment, the theaflavin used in the composition is extracted from black tea leaves. Tea leaf when picked from the tea plant contains polyphenols known as catechins. These catechins are colourless compounds. Theaflavins are produced during the oxidative fermentation of leaf tea to produce black tea. The preferred tea species for the purpose of this invention is selected from tea of the *Camellia sinensis* species. Aqueous extract of black tea which is fractionated to have higher levels of theaflavins is found to enhance the stability of dibenzoylmethane derivatives and Parsol-1789.

The black tea extract for the purpose of this invention comprises preferably 0.1 to 100%, more preferably 0.1 to 80% further more preferably 2 to 15% w/w of theaflavin. Such high values of theaflavin in black tea may be obtained by various processes disclosed by the present applicants in prior published patents e.g by tannase treatment. The composition according to the present invention comprises preferably 0.1 to 40%, more preferably 0.1 to 30% and further more preferably 0.1 to 10% w/w aqueous extract of black tea of the *Camellia sinensis* species.

Black tea in the normal course of manufacture typically comprises about 0.2 to 2% w/w of theaflavins. It is more often in the range of 1 to 2% w/w of the black tea. The theaflavin enriched fraction is preferably used in the composition of the present invention and is preferably prepared by solvent fractionation. Any suitable solvent e.g. alcohols, aromatic hydrocarbons, aliphatic hydrocarbons, ketones, esters, ethers, glycols, glycol ethers, alkyl halides, or aromatic halides can be used for the extraction process. The preferable solvents for examples are ethanol, ethyl acetate, chloroform, ethyl ether, n-butyl ether, tetrahydrofuran, acetone, methyl-iso-butyl ketone, toluene, methyl ethyl ketone, isopropyl myristate, phenoxy ethanol, fatty oils such as corn oil, soybean oil, olive oil, rape seed oil, cotton seed oil, sardine oil, herring oil, and whale oil.

The composition of the invention comprises 0.1 to 30%, preferably 0.3 to 10%, and further more preferably 0.45 to 5% theaflavin by weight of the composition.

The present inventors are aware that phenolic compounds have inherent antioxidant property. However several compounds having phenolic groups which are known antioxidants with antioxidant activities similar to theaflavins were tried by the present inventors as possible candidates for stabilizing sunscreens e.g. isobutein, methyl gallate, various green tea catechins, but they did not provide the stabilizing property that theaflavin was found to provide. Not wishing to be bound by theory the present inventors believe that theaflavin in the composition of the present invention provides the claimed benefit by virtue of a unique additional property of having high fluorescence quenching ability which may act by a singlet excited state quenching mechanism or by forming a complex with an excited species of dibenzoylmethane derivative. The above mechanisms are believed to far outweigh the well known antioxidant property of theaflavin in producing the desired benefits of the present invention.

A preferred composition of the invention is one where the weight ratio of dibenzoylmethane derivative to theaflavin is from 10:1 to 1:5.

The personal care composition comprises a cosmetically acceptable base. The cosmetically acceptable base may be a cream, lotion, gel or emulsion. An emulsion is preferred, a water-in-oil emulsion being more preferred. An especially suitable cosmetically acceptable base is one which comprises a water-in-oil emulsion comprising silicone oils as the continuous phase. The water in oil emulsions preferably comprise a crosslinked silicone elastomer blend.

It has been demonstrated by way of this invention that inclusion of a silicone elastomer blend in a water-in-oil emulsion improves the stability of the compositions prepared therewith. Unlike silicone fluids, silicone elastomers are cross-linked. The creation of cross-linkages between linear polymers, such as dimethicone, converts the linear polymer into a silicone elastomer. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions.

Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer]; EL-8050 [INCI Name: Isododecane (and) Dimethicone/Bis-Isobutyl PPG 20 Crosspolymer] DC 9040, DC 9041, DC 9045 (Dimethicone crosspolymer); DC 9506, DC 9509 (Dimethicone vinyl dimethicone crosspolymer); Shin-Etsu KSG-15, KSG-16 and KSG-17 (Dimethicone vinyl dimethicone crosspolymer). It is further preferred that the composition comprises a silicone based emulsifier.

Personal care compositions of the invention may be prepared using different cosmetically acceptable emulsifying or non-emulsifying systems and vehicles. A highly suitable base is an emulsion. Vanishing creams may also be used as a cosmetically acceptable base. Vanishing cream bases generally comprise 5 to 25% fatty acid and 0.1 to 10% soap.

The composition of the invention may additionally comprise a skin lightening agent. The skin lightening agent is preferably chosen from a vitamin B3 compound or its derivative e.g. niacin, nicotinic acid, niacinamide or other well known skin lightening agents e.g. aloe extract, ammonium lactate, arbutin, azelaic acid, kojic acid, butyl hydroxy anisole, butyl hydroxy toluene, citrate esters, 3 diphenyl propane derivatives, 2, 5 dihydroxybenzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

Useful inorganic sun-blocks are also preferably used in the present invention. These include, for example, zinc oxide, iron oxide, silica, such as fumed silica, and titanium dioxide.

Ultrafine titanium dioxide in either of its two forms, namely water-dispersible titanium dioxide and oil-dispersible titanium dioxide is especially suitable for the invention. Water-dispersible titanium dioxide is ultra-fine titanium dioxide, the particles of which are non-coated or which are coated with a material to impart a hydrophilic surface property to the particles. Examples of such materials include aluminium oxide and aluminium silicate.

Oil-dispersible titanium dioxide is ultrafine titanium dioxide, the particles of which exhibits a hydrophobic surface property, and which, for this purpose, can be coated with metal soaps such as aluminium stearate, aluminium laurate or zinc stearate, or with organosilicone compounds.

By "ultrafine titanium dioxide" is meant particles of titanium dioxide having an average particle size of less than 100 nm, preferably 70 nm or less, more preferably from 10 to 40 nm and most preferably from 15 to 25 nm.

By topical application to the skin of a mixture of both water-dispersible ultrafine titanium dioxide and oil-dispersible ultrafine titanium dioxide, synergistically enhanced protection of the skin against the harmful effects of both UV-A and UV-B rays is achievable.

Ultrafine titanium dioxide is the preferred inorganic sunblock agent as per this invention. The total amount of sunblock that is preferably incorporated in the composition according to the invention is from 0.1 to 5% by weight of the composition.

The composition according to the invention may also comprise other diluents. The diluents act as a dispersant or carrier for other materials present in the composition, so as to facilitate their distribution when the composition is applied to the skin.

Diluents other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Solvents, such as ethyl alcohol, isopropanol, acetone, ethylene glycol monoethyl ether, diethylene glycol monobutyl ether, diethylene glycol monoethyl ether;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The cosmetically acceptable base is usually from 10 to 99.9%, preferably from 50 to 99% by weight of the composition, and can, in the absence of other personal care adjuncts, form the balance of the composition.

The composition of the invention may comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition. Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% by weight of the composition and in many instances from 40 to 80%. Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C. Hydrophilic carrier liquids that can be employed in compositions herein commonly comprise water and/or a mono or polyhydric alcohol or water-miscible homologue. Monohydric alcohols often are short chain, by which is meant that they contain up to 6 carbons, and in practice is most often ethanol or sometimes iso-propanol. Polyhydric alcohols commonly comprise ethylene or propylene glycol, or a homologue can be employed such as diethylene glycol. Other than this suitable other vehicle and component used for deodorant composition can be added.

The compositions of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

The composition is formulated in any known format, more preferred formats being creams or lotions.

Now the invention will be demonstrated in terms of non-limiting examples.

Example 1

Parsol 1789 Stabilized with Theaflavin or Tea Extract Having Theaflavin

TF1 was obtained by treating a 1% w/w aqueous extract of black tea with 0.1% w/w tannase in water at 40° C. for about 3 to 4 hours. Then the resulting mixture was passed through styrene divinylbenzene (Diaion HP-20) and cross-linked hydroxyphopylated dextran (Sephadex LH-20) liquid chromatography columns and TF1 separated.

TF3 was obtained by treating tea leaves with epigallocatechin gallate and epicatechin in water under an air sparge and then passing the liquid phase of this mixture through a styrene divinylbenzene (Amberlite XAD1600) column eluted with a water/ethanol gradient mixture wherein the 95% v/v ethanol fraction was further purified by passing it through a crosslinked hydroxypropylated dextran (Sephadex LH-20) column eluted with ethanol to produce TF3 at greater than 95% purity.

TF4 was obtained in the same manner as TF3 except epicatechin was substituted by epicatechin gallate and the purity of the later fractions of eluant from the dextran column in TF4 increased to greater than 95%.

The method was based on spotting the HPTLC plates (in duplicate) with the sunscreen molecules of interest along with potential quencher molecules or formulations. The plate is then exposed to UVR (intensity 5.5 mW/cm$^2$) for 120 minutes. Following this the chromatographic separation was carried out using appropriate solvent system. Densitometry analysis is done to determine the amount of sunscreen degraded.

Stock solutions were prepared in methanol following the ratios as mentioned in the following table. 14 µL of stock solutions were loaded (3 mm width; 16 mm separation) on a 10×10 cm F254 HPTLC plate, using CAMAG LINOMAT 5 applicator equipped with a 100 µL micro-syringe (Hamilton, Switzerland). Ascending chromatography was performed at a distance of 85 mm in a TLC chamber using n-hexane-ethyl acetate 9:1 (v/v) as the mobile phase (~10 mL). The plates were dried at room temperature and subjected to ultraviolet absorption densitometry scan. The concentration dependent fluorescent bands due to presence of sunscreens were detected with a linear scan at 310 or 357 nm, using Camag TLC Scanner 3, in the presence of deuterium source. Slit width of 8×0.4 mm and scanning rate of 20 mm s$^{-1}$ were maintained during each densitometry scan. 4-t-buty-4'-methoxdibenzoylmethane concentrations present on each lane were determined from densitogram peak areas; prior and after the sun exposure using Win CATS Planar chromatography manager software. Results are presented in the following table:

TABLE 1

Ratios are given in weight

| Example No. | Samples | Mean Percent stability |
|---|---|---|
| 1a | Parsol 1789 | 61.9 |
| 1b | Parsol 1789 + Octocrylene—(1:1) | 75.3 |
| 1c | Parsol 1789 + Parsol MCX—(1:2) | 56.9 |
| 1d | Parsol 1789 + TF1—(1:1) | 90.3 |
| 1e | Parsol 1789 + TF3—(1:1) | 91.7 |
| 1f | Parsol 1789 + TF4—(1:1) | 93.9 |
| 1g | Parsol 1789 + Black tea ethyl acetate extract having ~9% of theaflavin—(1:4) | 75.9 |
| 1h | Parsol 1789 + Black tea ethyl acetate extract having ~62% of theaflavin—(1:2)† | 98.8 |

†Extract obtained from Hainan Groupforce Pharmaceuticals Co. Ltd.

In the above table TF1, TF3, TF4 are as defined earlier in detailed description.

900 kg Lipton Yellow Label black tea was subject to counter current extraction at 90-95° C. with water and then centrifuged. The liquid phase was subject to further purification using a ceramic membrane, ultrafiltration and reverse osmosis condensation, followed by ultra high temperature pasteurization and spray drying to yield 180 kg black tea aqueous extract (Tea extract 1) comprising 1% w/w theaflavin as measured by HPLC.

In the above example the black tea ethyl acetate extract was made in the following manner:

The black tea aqueous extract (Tea extract-1) (50 g) was dissolved in 500 mL of hot water at 70° C. The resulting aqueous solution was solvent extracted with chloroform (200 mL, 3 times). All chloroform fractions were pooled together and subjected to drying under vacuum (600-0.1 mb, 40° C.), to obtain a greenish-white coloured residue (3.0 g) enriched in caffeine. The aqueous layer was further solvent extracted with ethyl acetate (200 mL, 3 times). Ethyl acetate fractions were pooled together and subjected to drying under vacuum (100-0.1 mb, 40° C.), to obtain an orange-red coloured residue (4.0 g) enriched in theaflavin (6%) (Theaflavin enriched fraction 1, contains 9% TF).

The data in table 1 indicates that examples as per the invention (examples 1d, 1e, 1f, 1g and 1h) provide for vastly superior sunscreen stability as compared to examples outside the invention (examples 1a, 1b and 1c).

Example 2

Parsol 1789 Stabilization in a Composition with Tea Extract

For checking the stability the same procedure as stated in example 1 was followed. Only difference is, instead of the stock solution, here the formulation was taken directly. The following table represents the percent stability of Parsol 1789 in personal care compositions (as shown in table 3). The result has been reported as the percentage of Parsol 1789 remaining on the substrate after the indicated time. The black tea ethyl acetate extract of example 1 mentioned in this table has ~9% of theaflavin.

TABLE 2

Percentage stability of Parsol 1789

| Time (min) | Without tea extract (Example no. 2a) | 1.63% tea extract (Example no. 2b) | 5.2% tea extract (Example no. 2c) |
|---|---|---|---|
| 0 | 100 | 100 | 100 |
| 30 | 13.366 | 27.8 | 58.7 |
| 60 | 3.484 | 22.9 | 43.8 |

The data in table 2 indicates that personal care compositions as per the invention comprising black tea extracts comprising theaflavin have vastly enhanced sunscreen stability.

Example 3

Photoprotective Personal Care Vanishing Cream Base Composition with Tea Extract

The following table represents photoprotective personal care compositions made by using tea extract (9% of theaflavin).

TABLE 3

| Components | (Example no. 2a) Per 100 grams | (Example no. 2b) Per 100 grams | (Example no. 2c) Per 100 grams |
|---|---|---|---|
| Water | To 100 | To 100 | To 100 |
| Hystearic acid | 17 | 17 | 17 |
| Cetyl alcohol | 0.53 | 0.53 | 0.53 |
| IsoPropylMyristate | 1.64 | 1.64 | 1.64 |
| Parsol 1789 | 0.4 | 0.4 | 0.4 |
| Black tea ethyl acetate extract of example 1 (9% theaflavin) | 0 | 1.63 | 5.2 |
| Methyl paraben | 0.2 | 0.2 | 0.2 |
| Propyl paraben | 0.1 | 0.1 | 0.1 |
| Phenoxy ethanol | 4.4 | 4.4 | 4.4 |
| Glycerine | 1 | 1 | 1 |

TABLE 3-continued

|  | (Example no. 2a) | (Example no. 2b) | (Example no. 2c) |
|---|---|---|---|
| KOH (85%) | 0.56 | 0.56 | 0.56 |
| Disodium EDTA | 0.04 | 0.04 | 0.04 |
| Dimethicone | 0.5 | 0.5 | 0.5 |

Example 4

Photoprotective Hair Care Composition with Tea Extract

Parsol 1789™ along with theaflavin was also added in a hair care formulation. The hair care formulation was made in the form of a hair styling gel. Aristoflex AVC (cationic copolymer) was dissolved in water using a homogenizer. Parsol 1789™ and theaflavin were separately dissolved in propylene carbonate. The above two mixtures were then mixed and homogenized by using a high speed homogenizer. The composition is shown in table 4.

TABLE 4

| Ingredients | Percentage |
|---|---|
| Water | To 100 |
| Aristoflex AVC (cationic polymer) | 1.2 |
| Propylene carbonate (oil phase) | 9 |
| Parsol 1789 ™ | 1.2 |
| Theaflavin (62% enrich)† | 1.2 |
| Methyl paraben | 0.2 |
| Propyl paraben | 0.1 |

†Extract obtained from Hainan Groupforce Pharmaceuticals Co. Ltd.

Examples 5 to 8

Advantages of Compositions of the Present Invention Comprising a Cross Linked Silicone Elastomer Base Personal care compositions as shown in table 5 were prepared.

TABLE 5

|  | Example 5 (% w/w) | Example 6 (% w/w) | Example 7 (% w/w) | Example 8 (% w/w) |
|---|---|---|---|---|
| Parsol 1789 ™ | 0.81 | 0.81 | 0.44 | 0.44 |
| Black tea extract having ~62% theaflavin† | 0.00 | 1.62 | 0.00 | 0.89 |
| Phenoxy ethanol | 8.00 | 8.00 | 4.40 | 4.40 |
| Propylene carbonate | 8.00 | 8.00 | 4.40 | 4.40 |
| DC 5225C | 0.00 | 0.00 | 16.00 | 16.00 |
| DC EL8051 | To 100 | To 100 | 45.00 | 45.00 |
| Water | 0.00 | 0.00 | To 100 | To 100 |

†Extract obtained from Hainan Groupforce Pharmaceuticals Co Ltd.

For checking the stability, the same procedure as stated in example 1 was followed. The data on stability of the compositions of examples 5 to 8 is summarized in Table-6.

TABLE 6

| % of Parsol 1789 remaining | Example 5 (% w/w) | Example 6 (% w/w) | Example 7 (% w/w) | Example 8 (% w/w) |
|---|---|---|---|---|
| After 15 minutes | 62.6 | 98.8 | 54.0 | 77.1 |
| After 30 minutes | 49.0 | 95.00 | 40.4 | 68.0 |

The data in table 6 above indicates that compositions as per the invention (examples 6 and 8) provide for vastly improved stability of dibenzoyl methane sunscreen when theaflavin is added as a stabilizer in a cosmetically acceptable base comprising a silicone elastomer with or without silicone emulsifier, in comparison to control samples without theaflavin (examples 5 and 7).

Samples of example 2c (an oil in water emulsion) and example 6 (water in oil emulsion) were stored for studying the storage stability at a temperature of 25° C. It was observed that sample as per example 2c started to degrade after one week of storage while sample of example 6 did not show any degradation even after one month of storage.

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

The invention claimed is:

1. A personal care composition comprising:
   i) a dibenzoylmethane derivative;
   ii) 0.1 to 30% by weight theaflavin; and,
   iii) a cosmetically acceptable base,
   wherein the cosmetically acceptable base is a water-in-oil emulsion.

2. A composition as claimed in claim 1 comprising 0.3 to 10% theaflavin.

3. A composition as claimed in claim 1 wherein the dibenzoylmethane derivative is 4-t-butyl-4'-methoxydibenzoylmethane.

4. A composition as claimed in claim 2 comprising 0.1 to 10% dibenzoylmethane derivative by weight of the composition.

5. A composition as claimed in claim 1 wherein the theaflavin is selected from the group consisting of theaflavin, theaflavin-3-gallate, theaflavin-3'-gallate, theaflavin-3 and 3'-digallate.

6. A composition as claimed in claim 1 comprising an aqueous extract of black tea of the *Camellia sinensis* species comprising theaflavin.

7. A composition as claimed in claim 6 wherein the aqueous extract of black tea comprises 2 to 15% w/w theaflavin.

8. A composition as claimed in claim 6 comprising 0.1 to 40% aqueous extract of black tea of the *Camellia sinensis* species.

9. A composition as claimed in claim 1 wherein the weight ratio of dibenzoylmethane derivative to theaflavin is from 10:1 to 1:5.

10. A composition as claimed in claim 1 further comprising para-methoxy cinnamic acid or its derivatives.

11. A composition as claimed in claim 1 comprising 0.1 to 10% w/w of para-methoxy cinnamic acid or its derivatives.

12. A composition as claimed in claim 1 wherein the water-in-oil emulsion comprises a crosslinked silicone elastomer blend.

13. A composition as claimed in claim 1, wherein the composition provides superior chemical stability of the dibenzoylmethane derivative when exposed to ultraviolet radiation relative to the same composition but without the theaflavin.

* * * * *